United States Patent [19]
Manzone et al.

[11] Patent Number: 6,159,492
[45] Date of Patent: Dec. 12, 2000

[54] DRUG STORAGE AND DELIVERY SYSTEM CONTAINING A MEDICATED LOLLIPOP

[76] Inventors: Cheryl Manzone, 75-44 Grand Central Pkwy., Forest Hills, N.Y. 11375; Madeline Colussi, 157-34 Quince Ave., Flushing, N.Y. 11355

[21] Appl. No.: 09/262,246

[22] Filed: Mar. 4, 1999

[51] Int. Cl.$^7$ ........................................ A61K 9/68
[52] U.S. Cl. .................. 424/440; 424/439; 424/400; 206/828; 426/134
[58] Field of Search ........................... 424/439, 440, 424/400; 206/828; 426/134

[56] References Cited

U.S. PATENT DOCUMENTS

| | | | |
|---|---|---|---|
| 4,671,953 | 6/1987 | Stanley et al. | 424/440 |
| 5,615,941 | 4/1997 | Shecter | 362/109 |
| 5,855,908 | 1/1999 | Stanley et al. | 424/440 |

*Primary Examiner*—Dameron Jones
*Attorney, Agent, or Firm*—Anthony J. Casella; Gerald E. Hespos; Michael J. Porco

[57] ABSTRACT

A drug or other medication is incorporated into a candy and is molded onto a lollipop stick. A medicated lollipop is safely and conveniently stored by mounting the end of the lollipop stick remote from the medicated candy to the inner surface of a childproof cap. The lollipop then is inserted into a container, and the childproof cap is releasably locked with the open top of the container. The medicated lollipop can be accessed as needed merely by opening the container. Additionally, the medicated lollipop can be temporarily stored away from the container merely by converting the cap, and supporting the medicated lollipop by the cap.

5 Claims, 2 Drawing Sheets

DRUG STORAGE AND DELIVERY SYSTEM CONTAINING A MEDICATED LOLLIPOP

BACKGROUND OF THE INVENTION

1. Field of the Invention

The subject invention relates to an apparatus for safely storing a drug that has been incorporated into a candy product and for convenient delivery of that drug to a patient.

2. Description of the Related Art

Drugs typically are administered orally to patients. A typical drug is manufactured in a pill or capsule form, and a specified dosage of the pills and/or capsules are swallowed by the patient with a drink of liquid. Other drugs may be manufactured in a liquid form, and a selected dosage of liquid then is swallowed by the patient. Many patients have difficulties swallowing a pill or capsule. These difficulties may arise or become more acute when the patient is ill. In fact, the swallowing of a significant volume of water in an effort to consume a pill or the swallowing of a syrupy liquid drug may cause a violent intestinal reaction in a sick patient.

Lozenges are used to administer some soothing medications for patients who suffer from coughs or sore throats. However, neither lozenges nor other types of candies are used very often to administer other types of drugs. In this regard, pharmaceutical companies and the health profession have been reluctant to incorporate drugs into a candy form due to the risk of having a child mistake the candied form of drug for a non-medicated confectionery product.

Lollipops can be a convenient vehicle for administering a drug to a patient. In particular, a lollipop differs from a lozenge in that the stick on a lollipop enables the lollipop to be temporarily removed from the patient's mouth. This enables the patient to communicate orally when necessary. The ability to communicate clearly is extremely important to many working adults who must periodically take medication while at their place of employment. However, a medicated lollipop mistakenly could be confused for a non-medicated candy, and could be consumed by a child. The medication in the lollipop would not be needed by the child and could be harmful to the child. As a result, lollipops are not well suited for the delivery of medication to patients without a safety precaution for preventing inadvertent consumption of a medicated lollipop by a child. Additionally, it would be desirable to provide the ability to safely and conveniently store portions of the medicated lollipop prior to complete consumption.

Copending application Ser. No. 09/189,246 was filed by Cheryl Manzone and discloses various structures to permit the candy portion of a lollipop to be temporarily supported in spaced relationship to a support surface. Thus, an adult consuming such a lollipop could temporarily remove the lollipop from his or her mouth and support the lollipop temporarily on a desk or table while the person conducts a conversation over a telephone. Upon completion of the telephone conversation, the person may resume consumption of the lollipop. Although the invention disclosed in the copending application enables significant efficiencies, there is little security that would make the lollipop well suited for medicated products that should be kept from children.

In view of the above, it is an object of the subject invention to provide an apparatus for efficient delivery of medication in a lollipop form.

It is another object of the subject invention to enable safe, virtually childproof storage of a medicated lollipop.

It is an additional object of the subject invention to provide a lollipop that can easily be supported with the candy spaced from the supporting surface so that the lollipop may be consumed on an interrupted or intermittent basis.

SUMMARY OF THE INVENTION

The subject invention relates to a medicated lollipop. The lollipop includes a stick having opposed ends. A medicated candy is securely attached to one end of the stick. The apparatus further includes a safety container having a closed bottom and a continuous sidewall extending upwardly from the closed bottom. Portions of the sidewall remote from the bottom define an open mouth. The mouth includes a locking structure extending thereabout. For example, the locking structure may include an annular rim or an array of threads. The mouth of the container is sufficiently wide to enable the medicated candy to be passed therethrough. Additionally, the mouth of the container is spaced sufficiently from the bottom wall of the container to permit the entire lollipop, including the candy and the stick to be received in the container.

The apparatus further includes a safety cap that is releasably lockable over the mouth of the container. The releasable locking is configured to be substantially childproof. Thus, the releasable locking of the cap may include an array of threads that require simultaneous axial movement of the cap relative to the container and a torsional movement thereof. Alternatively, the releasable locking may include a projection on the cap that must be aligned with a notch on the mouth of the container to enable a snapped removal of the cap from the container. Such childproof releasable locking of caps and containers may be one of the many available combinations that are common in the prior art.

The cap includes an inner surface that faces the opening of the container when the cap is releasably engaged on the container. The end of the lollipop stick remote from the medicated candy extends from the inner surface of the cap. Thus, the medicated candy on the lollipop can be accessed only by releasing the childproof locked engagement of the cap from the container. This separation of the cap from the container provides convenient access to the lollipop, and the lollipop can be consumed by the patient while the cap remains affixed to the end of the lollipop stick remote from the medicated candy. The lollipop may be temporarily stored prior to complete consumption merely by supporting the lollipop by the cap of the apparatus, such that the outer face of the cap is placed on a supporting surface and such that the lollipop stick and the medicated candy project upwardly therefrom. This temporary storage might be used, for example, if the person consuming the medicated candy on the lollipop needs to receive or place a telephone call that requires an ability to speak clearly and without interference by the candy. Longer terms for more secure storage of the medicated candy can be achieved merely by inserting the partially consumed medicated candy back into the container and reattaching the cap to the open mouth of the container.

The container and/or the cap may be provided with a carrying handle or strap to enable convenient carrying of the medication. This may be particularly helpful for old or very ill patients who might otherwise have difficulty carrying or manipulating a small container or a lollipop attached to a small cap.

The container may be a double-ended container having a top opening, a bottom opening and an intermediate wall therebetween. The intermediate wall may isolate portions of the container that are accessible at the top opening from portions of the container that are accessible at the bottom opening. Both the top and bottom openings may include safety caps, such as a pry-off cap that requires specified rotational alignment before the cap can be pried free of the container or a press and turn threaded cap. The top part of the container may be used for storing a medicated lollipop as described above. The bottom part of the container may be used to store orally consumable capsules. A container of this type is particularly useful in view of the fact that many patients must take more than one type of medication. Additionally, some medications, such as pain medicine, can be delivered very efficiently with a medicated lollipop, whereas other medications are delivered more efficiently through a conventional capsule.

The container may be provided with a clip or clamp which permits the container to be releasably engaged to a location near the patient. For example, the container may be snapped into engagement to a bed rail or may be clipped to a portion of a blanket. The feature of the clip ensures that medication can be maintained in close proximity to the patient.

DETAILED DESCRIPTION OF THE PREFERRED EMBODIMENT

Figure 1:
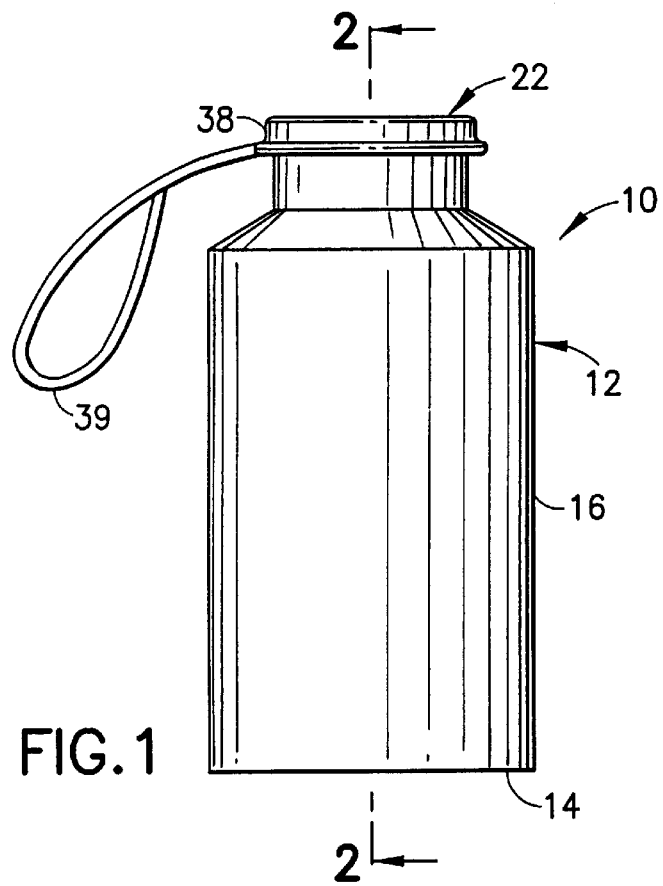
FIG. 1 is a side elevational view of a container in accordance with the subject invention.
Figure 2:
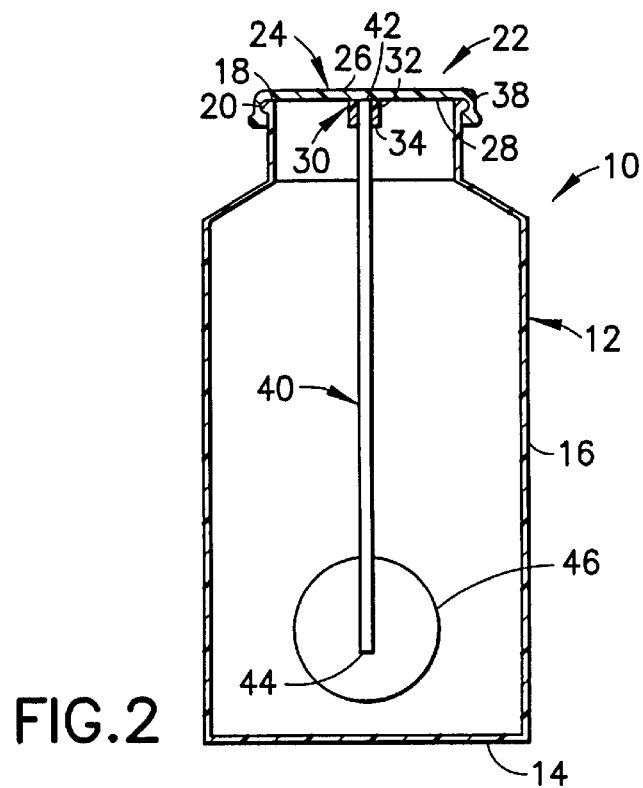
FIG. 2 is a cross-sectional view taken along line 2—2 in FIG. 1.

A medication storage and delivery apparatus in accordance with the subject invention is identified by the numeral 10 in FIG. 1. The apparatus 10 includes a container 12 having a closed bottom 14 and a continuous rigid sidewall 16 extending upwardly from the bottom 14. As shown herein, the sidewall is substantially cylindrical, but other shapes may be provided. The sidewall extends to an open mouth 18 at the end of the sidewall 16 remote from the bottom 14 of the container 12. The mouth 18 is characterized by a substantially annular lip 20 extending substantially circumferentially around the mouth 18. However, the lip 20 includes an interruption into which a projection on a cap can be received for removing or replacing the cap as explained further below.

The apparatus further includes a cap 22 having a top wall 24 that is sufficiently large diametrically to cover the open mouth 18 of the container 12. The top wall 24 includes an outer surface 26 and an inner surface 28. A stick support 30 is formed centrally on the inner surface 28 of the top wall 24 of the cap 22. The stick support 34 includes a cylindrical sidewall 32 having an open edge 34 remote from the top wall 24. A plurality of resiliently deflectable fingers extend inwardly from the open end 34 of the cylindrical sidewall 32 and toward the top wall 24 of the cap 22.

The cap 22 further includes an annular skirt 38 extending downwardly from outer portions of the top wall 24 and in substantially concentric relationship with the stick support 30. A skirt 38 defines an inside diameter that is equal to or slightly less than the outside diameter of the bead 20 around the open top 18 of the container 12. However, the skirt 38 further includes an inward projection to provide a significant interference with the bead 20. Thus, the projection on the skirt 38 must be aligned with the notch formed in the bead 20 for facilitating mounting of the cap 22 on the container 12 or the removal of the cap 22 therefrom. The interengagement of the projection on the skirt 38 of the cap 22 with the rim 20 on the container 12 is known in the art and is provided on many commercially available medicine containers. The need to initially align the projection with the nut renders the combination of the cap 22 and container 12 substantially childproof. Other such known childproof releasable locks can be provided in the apparatus of the subject invention. The cap 22 may further be provided with a carrying strap 39 to facilitate carrying or other such digital manipulation of the cap. The strap 39 can be substantially longer than shown and can be looped around a wrist or belt to ensure that the drug remains in proximity to the patient.

The apparatus further includes a lollipop stick 40 having opposed ends 42 and 44. The end 42 of the lollipop stick 40 is lockingly engaged by the resiliently deflectable fingers 36 on the stick support 30 of the cap 22. The end 44 of the stick has a medicated candy 46 molded thereon. The candy defines an outside diameter that is smaller than the inside diameter of the open mouth 18 of the container 12. Additionally, the stick 40 and the candy 46 define an overall length that is less than the height of container 12, as measured from the closed bottom 14 to the open mouth 18. With this construction, the cover 22 can be releasably locked on the container 12 with the stick 40 and medicated candy 46 securely retained therein. This secure retention of the medicated candy 46 in the container 12 is substantially childproof. Additionally, the medicated candy can be maintained substantially sterile and substantially free of moisture. If necessary, the medicated candy can be wrapped more securely within the container. Thus, the container provides childproof features for the medicated candy, while the inner wrapping on the medicated candy provides sterility and long term shelf life.

Medicated candy can be accessed merely by manipulating the cover 22 and the container 12 in an appropriate manner for removing the cover 22 from the container 12. Thus, in the particular embodiment shown herein, the cover 22 is rotated sufficiently from the projection from the skirt 38 to align with the notch in the bead 20. An upward prying force then is exerted on the cover 22 to enable the cover 22 to be resiliently biased passed the rim 20 of the cap 12. Complete separation of the cover 22 then enables the lollipop stick 40 and the medicated candy to be removed from the container 12. If necessary, a sterile wrapping over the medicated candy 46 can be removed, and the medicated candy can be consumed by a patient. Consumption of the medicated candy does not require the sometimes difficult task of swallowing a pill or capsule and does not require the consumption of a significant volume of water that could make the patient ill.

Figure 3:
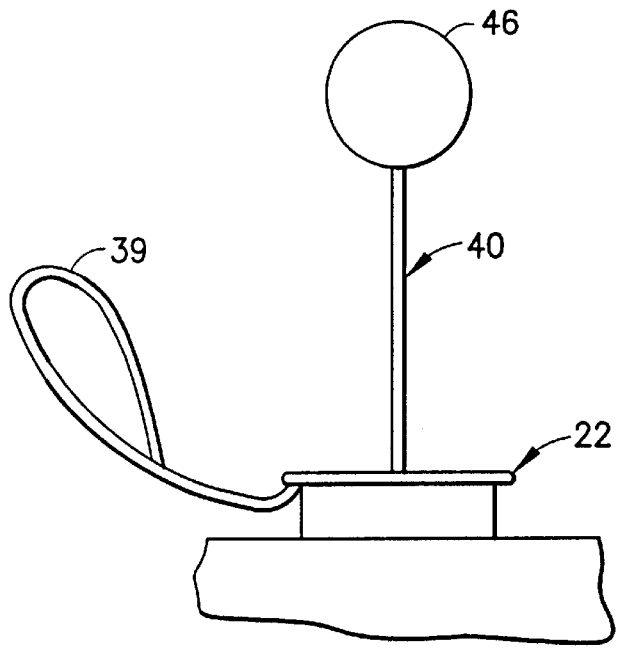
FIG. 3 is a side elevational view of the cap and lollipop separated from the container and temporarily stored in an upright orientation.

The patient can temporarily store the medicated candy merely by supporting the medicated candy by the cap, as shown in FIG. 3. Alternatively, the patient can reinsert the partly consumed medicated candy back into the container and can releasably lock the cover 22 back onto the container. The remainder of the medicated candy can be consumed at a later time.

Figure 4:
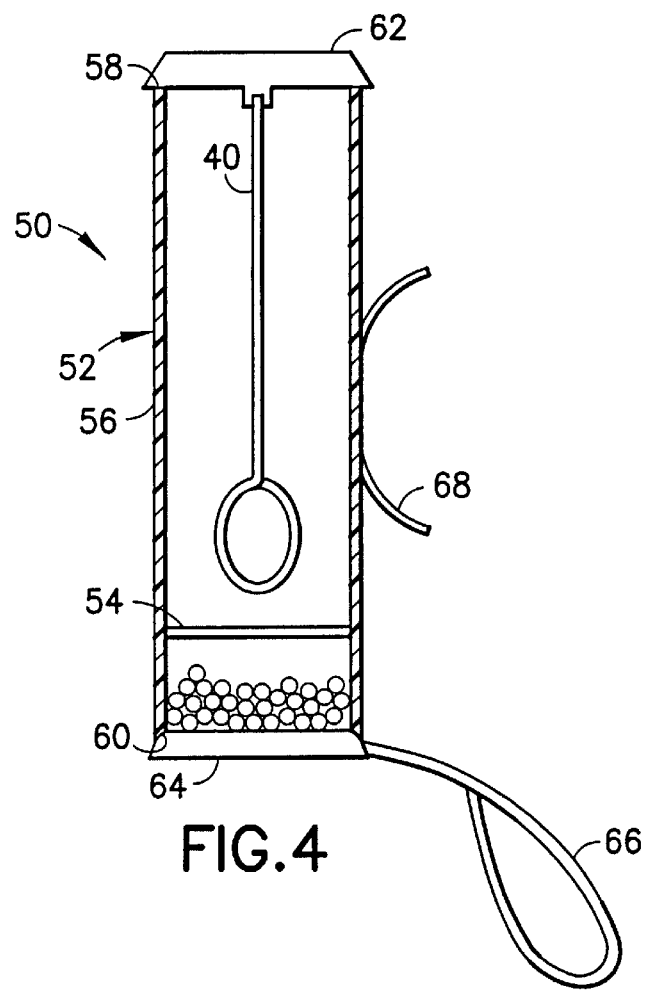
FIG. 4 is a side elevational view, partly in section, of an alternate container in accordance with the subject invention.

FIG. 4 shows an alternate embodiment. More particularly, FIG. 4 shows a medication storage and delivery apparatus which is identified generally by the numeral 50. The apparatus 50 includes a container 52 having a bottom wall 54 and a tubular sidewall 56 extending in both directions from the bottom wall 54. The tubular sidewall 56 includes a first opening 58 on one side of bottom wall 54 and a second opening 60 on the opposed side of the bottom wall 54. A first safety cap 62 is mounted to the container 52 at the first opening 58. A second safety cap 64 is mounted to the container 52 at the second opening 60. The first safety cap 62 is substantially identical to the cap 22 described and illustrated above. In particular, the first safety cap 62 is configured to accommodate a medicated lollipop 40. The second safety cap 64 is of conventional construction and is used to safely store orally consumable tablets or capsules in the space bounded by the bottom wall 54 and the sidewall 56 and the safety cap 64.

The second safety cap 64 is provided with a carrying strap 66 comparable to the carrying strap 39 described and illustrated above. The provision of the carrying strap 66 at a location spaced from the first safety cap 62 avoids the potential inconvenience of the carrying strap on or near the portion of the medicated lollipop that will be held and consumed by a patient.

The sidewall 56 of the container 52 is further provided with a clamp 68 dimensioned and configured to permit the container 52 to be releasably engaged to a bed rail of a hospital bed. Thus, the patient can be ensured of having the container in close proximity at all times.

While the invention has been described with respect to a preferred embodiment, it is apparent that various changes can be made without departing from the scope of the invention as defined by the appended claims. For example the lollipop stick may be unitarily molded with the cap. Additionally, the cap may be engageable on the container by other childproof means, such as a press-and-turn threaded connection or a shrink-wrap protection. These and other changes will be apparent to a person skilled in the art after having read this disclosure.

What is claimed is:

1. An apparatus for storing and delivering a medicated product, said apparatus comprising:

a container having a closed bottom, a sidewall structure extending rigidly upward from the closed bottom and an open mouth remote from the closed bottom, the container including a releasable locking structure extending substantially around the open mouth thereof;

a cap having a top wall with a top surface and a bottom surface, the top wall being dimensioned to substantially close the open mouth of the container, a skirt projecting downward from the top wall and being released with the open mouth of the container; and a lollipop having a stick with a first end secured in the inner surface of the top wall of the cap and a second end, a medicated candy secured to the second end of the stick, the candy and stick being dimensioned to be removed from the container when the cap is released on the open mouth of the container.

2. The apparatus of claim 1, wherein the cap includes a stick support formed on the inner surface of the top wall of the cap, the stick support being configured for securing the stick therein.

3. The apparatus of claim 2, wherein the stick support includes a substantially cylindrical wall projecting downward from the inner surface of the top wall of the cap and a plurality of resiliently deflectable locking fingers projecting inward and upward from the cylindrical wall for securing portions of the stick inserted therein.

4. The apparatus of claim 1, wherein the stick is unitary with the cap.

5. The apparatus of claim 1, wherein a flexible strap extends from the handle.

\* \* \* \* \*